US000001386H

United States Statutory Invention Registration [19]

[11] Reg. Number: H1386

Testa et al.

[43] Published: Dec. 6, 1994

[54] ALUMINUM COMPLEXES USEFUL FOR CROSS-LINKING COATING COMPOSITIONS

[75] Inventors: Carlo A. Testa, Macclesfield; David G. Davenport, Swinton, both of United Kingdom

[73] Assignee: Rhone-Poulenc Chemicals Limited, Watford, United Kingdom

[21] Appl. No.: 95,226

[22] Filed: Jul. 23, 1993

[30] Foreign Application Priority Data

Jul. 24, 1992 [GB] United Kingdom ..... 9215795

[51] Int. Cl.[5] ..... C08F 20/00; C07F 5/06

[52] U.S. Cl. ..... 525/437; 556/179; 556/182; 556/183; 554/76

*Primary Examiner*—Robert L. Stoll
*Assistant Examiner*—Joseph D. Anthony
*Attorney, Agent, or Firm*—Finnegan, Henderson, Farabow, Garrett & Dunner

[57] ABSTRACT

Aluminum complexes useful as cross-linking agents for coating compositions, especially high solids compositions containing an alkyd resin binder, are made by reacting a volatile oxime with a product of reaction of (1) an aluminum alcoholate or phenolate, (2) a carboxylic acid and/or $\beta$-diketo compound, and (3) optionally water.

5 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

ALUMINUM COMPLEXES USEFUL FOR CROSS-LINKING COATING COMPOSITIONS

This invention relates to aluminum complexes useful for cross-linking coating compositions, and more particularly to aluminum complexes which are useful as driers and in some cases also rheology modifiers, in coating compositions of high solids content.

Conventional alkyd paint systems involve the use of substantial amounts of organic solvent, e.g. white spirit. To reduce the amount of solvent required, coating compositions of high solids content have been developed. Certain technical problems are involved. More particularly, conventional alkyd resins used in paints are of high molecular weight and only relatively few functional groups per molecule are required to form satisfactory cross-linked films. High solids content paint systems, on the other hand, require the use of lower molecular weight binders (so that the composition shall have a sufficiently low viscosity for ease of application), and for this reason a substantially larger number of functional groups must be present per molecule so that the final cross-linked film shall have the required high molecular weight.

Conventional alkyd paint films cross-link by reactions involving oxidation and polymerization of the unsaturated alkyl groups present in the drying oils used in making the alkyd resin. The drying process involves reaction of the film with atmospheric oxygen, and to promote this reaction metallic soaps (driers) are incorporated in the paint composition. Cobalt and manganese soaps are effective at accelerating the surface drying of a paint film but are less effective in promoting uniform drying through the thickness of the coating. Lead driers are very effective for promoting drying through the thickness of the film, but it is desirable to eliminate them from paint systems because of the inherent toxicity of lead. For this purpose, zirconium has been proposed as a replacement for lead because of its low toxicity. Zirconium promotes through drying of the paint film by coordination bonding. However, in high solids coatings, levels of cobalt, zirconium and calcium driers which are satisfactory in conventional alkyd paint systems are insufficiently effective to produce through drying. Consequently, to improve through drying, manufacturers of high solids coating compositions have recommended increasing the zirconium level from the standard level of about 0.09% up to 0.6% zirconium, and such higher levels of zirconium or other metal driers and other agents, especially chelating agents, are incorporated into alkyd resin based coating compositions of high solids content. The purpose of the chelating agents is to form soluble coordination complexes with the drier metals and such complexes are generally found to be more effective as driers than uncomplexed metal salts. The usual chelating agents incorporated in coating compositions for this purpose are 1,10-phenanthroline and 2,2'-dipyridyl. However, in some cases even the use of high levels of zirconium or other drier metals, with or without a complexing agent, still does not produce adequate drying of the coating composition. There is therefore a need for more effective drier systems. Moreover, the cost of using high levels of zirconium and chelating agent is itself a drawback in existing drier systems for compositions of high solids content. Chelating agents may also give rise to discoloration of the paint film.

The rheology of coating compositions of high solids content also causes problems. In a conventional alkyd based coating composition, when the solvent evaporates, the alkyd resin left behind is very viscous and has only limited tendency to flow. However, with coating compositions of high solids content, the resins left behind after evaporation of the solvent are much less viscous and frequently flow in an undesirable way to produce the problems of sagging and dripping. To reduce these problems, it is necessary to incorporate in the composition a rheology control additive. An additive which promotes thixotropy in the composition reduces sagging and dripping, but thixotropic additives are frequently ineffective in coating compositions of high solids content and it is necessary to introduce into the composition a degree of pseudoplasticity. High solids paint compositions formulated with a pseudoplastic component can be made so that sagging and dripping are eliminated. However, a paint having a pseudoplastic rheology has other undesirable properties. In particular, such paints are difficult and tiring to brush out because of the much higher viscous drag on the paint brush. Also, pseudoplastic paints, unlike thixotropic paints, reform their structure immediately on brushing out so that brush marks are retained in the applied coating. It is therefore desirable to be able to produce a high solids coating composition which becomes pseudoplastic only after it has been applied. In this way, it would be possible to provide a paint which would not exert undesirable viscous drag on the paint brush or leave brush marks on application, but would nevertheless not sag or drip after application.

Other metals have been proposed for use as driers in high solids coating compositions. For example, International specification WO91/15549 proposes the use of neodymium carboxylates to improve through drying in high solids content coating compositions. It is stated that a level of 0.1 to 0.4% neodymium combined with cobalt significantly improves drying, especially in thick films, when compared with zirconium, lanthanum or cerium even at high levels. This improvement is more pronounced when vanadium and potassium carboxylates and complexing agents such as 2,2'-dipyridyl are used. With a particular high solids alkyd resin (Beckosol 10-539), a combination of cobalt, neodymium, vanadium, potassium and 2,2'-dipyridyl is recommended. However, neodymium is expensive and "loss of dry" (i.e. loss of drying capacity on storage) may be unsatisfactory with the combination of neodymium, cobalt, vanadium, potassium and 2,2'-dipyridyl proposed in this specification.

Coating compositions contain resins which have functional groups such as carboxyl and hydroxyl groups, which have free electron pairs able to form coordinate linkages with metals such as zirconium; this coordinate bonding is an essential feature of the drying of the resin. It is known that aluminum compounds can form coordinate linkages with free electron pairs present in the resins used in surface coatings, and such compounds have been proposed as replacements for lead and zirconium driers. For example, aluminum alkoxides, substituted alkoxides and polyoxo-aluminum compounds as disclosed in British Specification No. 825878 and European Patent Specification 0018780 may be used. However, these aluminum compounds are of only limited utility both in conventional an in high solids alkyd resin-based coating compositions because aluminum has very high affinity for the free carboxyl, hydroxyl and other groups in the resins capable of forming coordinate or covalent linkages. While this affinity is desirable in drying, it is undesirable while the coating composition is being stored and frequently causes gelling of the composition which renders it unusable. The polyoxo aluminum compounds disclosed in European Specification 0018780 have a reduced tendency to form such gels, especially with resins which contain relatively small proportions of functional groups and have relatively low molecular weight, but even these compounds do not always provide compositions of adequate stability on storage. It has also been observed that embrittlement of the film takes place on ageing.

Various methods have been proposed for solving the problems caused by the high reactivity of aluminum driers. One method is to provide the composition as two packs so that the aluminum compound is kept separate from the resin until the coating composition is required for use. However, this is an inconvenient solution, and the coating composition, once mixed, must be used without delay. Another method is to dilute the composition containing the aluminum compound and the resin with solvent until it has an acceptable viscosity for application. This is, however, inconvenient and wasteful of solvent, and produces variable results.

It has also been proposed to reduce the acid value of resins which, because of their acid content, tend to react rapidly with aluminum compounds, by esterifying the free carboxyl groups by reaction with an oxirane compound, e.g. ethylene oxide, propylene oxide, epichlorohydrin, methyl glycidyl ether, phenyl glycidyl ether, glycidyl ethyl hexoate, glycidyl versatate, glycidyl hydroxide and epoxidized fatty ester. However, this does not sufficiently reduce the reactivity of the resins and this additional reaction may undesirably affect the performance of the coating composition.

European Patent Specifications 0148636A and 01048637A propose to produce stable compositions in which the aluminum compound is stabilized by addition of a volatile base and water. The resulting systems are stated to be more storage stable. The presence of water is believed to inhibit reaction between alkoxide groups attached to aluminum and hydroxyl groups present in the film-forming resin. The volatile base neutralizes free carboxyl groups present in the resin and thus prevents them from reacting with alkoxide groups in the aluminum compound during storage. When the coating composition is used, the volatile base evaporates and allows the carboxyl groups thus released to interact with the aluminum compound. This allows crosslinking to take place and acceptable through drying of the coating to be obtained. The volatile base used should have an acceptable odor and toxicity, and it is stated that dimethylaminoethanol is preferred. However, even dimethylaminoethanol has an odor which is unacceptable in enclosed areas, and the compositions are thus not acceptable for interior decorating. Moreover, in practice, not all the amine evaporates and any amine remaining in the dried coating is liable to cause yellowing.

The present invention provides a novel type of aluminum complex which can be incorporated into coating compositions, especially compositions of high solids content, to act as driers which improve, more particularly, the through drying of the coating. These new aluminum complexes have a reduced tendency to react with the resin in the coating composition during storage. Their use involves considerable cost savings as compared with the use of drier systems based on zirconium or neodymium. They impart little or no odor and do not cause yellowing in coatings containing them. The level of drying of the coatings obtained is satisfactory both on the surface and through the coating, and the films do not tend to become brittle with age.

The aluminum complexes of the present invention are formed by reaction of a volatile ketoxime or aldoxime with an aluminum product obtained by reaction of (i) an aluminum alcoholate or phenolate with (ii) an enolizable $\beta$-diketo compound and/or a carboxylic acid and (iii) optionally water. The proportion of the volatile ketoxime or aldoxime used is preferably calculated to be at least sufficient to complex all the unoccupied aluminum coordination sites in the aluminum product, but lower levels do show some benefits insofar as they reduce the activity of the aluminum product. The inclusion of the volatile complexing agent effectively prevents free coordination sites on the aluminum compounds from reacting with functional groups present in the coating resin. When the composition is applied, the volatile ketoxime or aldoxime evaporates and the aluminum is then able to react with the functional groups in the resin and promote through drying of the coating.

The volatile ketoxime or aldoxime used in forming the complexes of the invention is preferably a linear, branched or cyclic ketoxime or aldoxime containing 2 to 6 carbon atoms, e.g. butyraldehyde oxime and cyclohexanone oxime, but methylethylketoxime is preferred. This compound is known for use in paint formulations as an anti-skinning agent or stabilizing agent. For this purpose it is used in a proportion of 0.1 to 0.4% by weight of the coating, and it has no reported effect on the performance of the paint. It will be appreciated that the purpose of such oximes when used in the present invention is completely different. As used herein, the oxime effectively deactivates the aluminum complex during storage of the coating composition. When the latter is used, the oxime evaporates and the aluminum compound is reactivated. The proportion of oxime used in the coating compositions produced in accordance with the present invention is significantly more than the proportion heretofore used in coating compositions where it is added to the composition as a whole and not specifically to any aluminum drier which may be present. It will be appreciated in this connection that, for the purpose of the present invention, sufficient of the oxime should be present in the aluminum complex to complex all the aluminum coordination sites which are present. If such sites are allowed to remain, the danger of the coating composition gelling on storage remains.

It is a further advantage of the complexes of the present invention that they have no unacceptable odor.

Surprisingly, it has been found that in some preferred embodiments of the present invention a high solids coating composition can be obtained with improved sag and drip resistance. It is believed that when a coating composition in accordance with the present invention is applied and the solvent and oxime evaporate, the aluminum then reacts rapidly with the functional groups present in the alkyd resin and atmospheric moisture providing cross-linking and producing a pseudoplastic coating. The rheology of the coating is possibly similar to that produced by organic aluminum compounds in printing inks where they are used to impart pseudoplasticity so as to increase dot sharpness in printed stock. This introduction of pseudoplasticity to the coating after the coating composition has been applied has the advantage that additives may still be included in the composition in order to make it thixotropic for optimum application properties. The composition may then be applied satisfactorily to a vertical substrate with no viscous drag, and the pseudoplastic condition which arises after evaporation of the solvent and oxime then reduces or eliminates sagging and dripping.

The new aluminum complexes may be used in coating compositions at aluminum levels rather lower than those which have previously been used. In known aluminum containing compositions, the proportion of aluminum is typically 0.5 to 2% by weight of the binder. At higher aluminum contents within this range embrittlement of the dried coating on ageing is likely to occur, probably caused by continued cross-linking of the aluminum with the resin. When the aluminum complexes of the present invention are used, the proportion of aluminum is usually in the range 0.05 to 0.2%, typically about 0.1%, based on the binder content. This reduces the possibility of continued cross-linking with time and coatings produced using the new aluminum complexes have not been observed to become brittle with age.

In some cases, coating compositions formulated with the new aluminum complexes have been found to have a reduced rate of surface drying. To overcome this, more cobalt and lithium can be incorporated into the composition. The extra cost involved in this is not however significant and is less than would be involved in using a zirconium or neodymium drier.

The aluminum products with which the ketoxime or aldoxime is reacted to produce the aluminum complexes of the invention are of two different kinds depending on whether water is, or is not, used in making the product.

When water is used, the aluminum products are essentially as described in European specification 0018780. They are made by reacting together an aluminum alcoholate or phenolate, an enolizable β-diketo compound and/or a carboxylic acid, and water. According to the said European specification, these products may be represented by the formula:

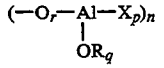

wherein —O— is an oxygen atom bridging two aluminum atoms; —OR is an alkoxy group where R is an optionally substituted alkyl group containing from 1 to 4 carbon atoms or an alkoxyalkyl group containing 4 to 6 carbon atoms; —X is a substituent derived by elimination of a hydrogen atom from an enolate or a mixture of substituents comprising at least one substituent derived by elimination of a hydrogen atom from an enolate and one or more substituents derived by elimination of a hydrogen atom from an alcohol containing more than 4 carbon atoms, a phenol, a carboxylic acid, a mono-ester of a dicarboxylic acid or a di-ester of a tri-carboxylic acid or a hydroperoxy compound; p+q are independently numbers greater than 0 with the proviso that p+q is less than 3; r is a number represented by the relationship $$\frac{3-p-q}{2}\text{; and}$$

n is a number of 2 or more.

For the purposes of the present invention, this formula is conveniently rewritten as the average formula

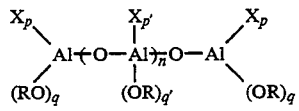

where X is a substituent derived from the enol form of an enolizable β-diketo compound by removal of a hydrogen atom or a carboxylate residue or a mixture of both, R is the residue of an alcohol or phenol of formula R—OH, each of p and q is greater than 0 and less than 2 such that (p+q)=2, p′ is greater than 0 up to 1 and q′ is from 0 to less than 1 such that (p′+q′)=1, and n is 0 or more. Preferably X is an ethylacetoacetate residue and R=isopropyl or X is an octylacetoacetate residue and R=isobutyl.

These products may be made by the reaction together of an aluminum alcoholate or phenolate of formula $Al(OR)_3$ with an enolizable β-diketo compound and/or a carboxylic acid, and water. An appropriate solvent, more particularly an alcohol or phenol of formula ROH, may be present. Preferably an aluminum alcoholate derived from an alcohol of 1 to 4 carbon atoms or an alkoxy alcohol of 4 to 6 carbon atoms is used. Preferred such alcohols are isopropanol, 2-butanol and ethoxyethanol.

The β-diketo compound is preferably an ethyl or higher ester of acetoacetic acid, e.g. ethyl acetoacetate, acetylacetone or other β-diketone, diethyl malonate, or another malonic acid ester.

The carboxylic acid may be any saturated or unsaturated aliphatic or cycloaliphatic acid or aromatic acid of up to 25, preferably 6 to 25, carbon atoms. Suitable such acids include neodecanoic acid, soya oil fatty acid, erucic acid, linoleic acid, oleic acid, benzoic acid and 2-ethyl-hexanoic acid.

Reference may be made to the aforesaid European specification 0018780 for a description how these aluminum-containing products are made.

Alternatively, if the product is made without inclusion of water in the reaction mixture, the aluminum-containing products may be represented by the average formula:

$$Al(OR)_q(W)_n(X)_p$$

where R is the residue of an alcohol or phenol of formula R—OH, W is substituent derived from an enolizable β-diketo compound by removal of a hydrogen atom, X is a carboxylate residue, n, q and p are each 0 to 3 such that (q+n+p)=3. In a preferred example W is an acetylacetonate residue q=0, X is a soya oil fatty acid residue, n=0.2, and p=2.8. Also preferred are: W=stearoyl benzoyl methane residue, n=3, and p=q=0; W=octyl acetoacetate residue, n=3, and q=p=0; W=acetylacetone residue, X=erucic acid residue, n=0.2, p=2.8, and q=0; and R=isobutyl, W=ethyl acetoacetate residue, q=2, n=1 and p=0.

The aluminum alcoholate or phenolate, the β-diketo compound, and the carboxylic acid used in making products of this formula may be the same as those used in making the products formed in the presence of water.

Whichever type of aluminum-containing product is used, the proportion of volatile ketoxime or aldoxime complexed with the aluminum should be up to 3 molecules per aluminum atom. Additional oxime can be used if required, and the excess then acts as a diluent and improves the stability of the complex.

The following examples describe the preparation of the aluminum-containing products.

EXAMPLE 1

| | |
|---|---|
| Aluminum tri-isopropoxide | 102 g |
| Propan-2-ol(1) | 25 |
| Acetyl acetone | 25 |
| Soya oil fatty acid | 337.5 |
| Propan-2-ol(2) | 25 |
| Propan-2-ol(3) | 25 |
| Methylethylketoxime | 261.4 |

The aluminum tri-isopropoxide and propan-2-ol(1) were charged to a flask fitted with a stirrer, thermometer, nitrogen purge and a condenser for refluxing and distillation. Stirring was commenced and the solution was heated to 50° C. The acetylacetone was then added via a dropping funnel (over 5 mins.). The exothermic reaction caused the temperature to rise to 58° C. The mixture was further heated to 80° C. A solution of soya oil fatty acid in propan-2-ol(2) was added by a dropping funnel over a period of 30 minutes, maintaining the temperature of the reaction mixture at 80° C.

The dropping funnel was flushed with propan-2-ol(3) and the washings transferred to the flask. The mixture was heated to reflux and held for one hour. The apparatus was set up for distillation and heated. Distillation commenced at 92° C. and was continued at atmospheric pressure until 137° C. was reached. The flask was then cooled to 105° C. and vacuum was applied with heating until distillation ceased at 110° C. The product was cooled to 70° C. and the methylethylketoxime was added during a 5 minute period via a dropping funnel.

EXAMPLE 2

Example 1 was repeated but using 391.2 g of the soya oil fatty acid and 10 g of acetylacetone.

EXAMPLE 3

Example 1 was repeated using 285 g of cekanoic acid (in place of the soya oil fatty acid) and no acetylacetone.

EXAMPLE 4

Example 1 was repeated using 395.5 g of oleic acid (in place of the soya oil fatty acid) and 10 g of acetylacetone.

EXAMPLE 5

Example 1 was repeated using 216 g of 2-ethyl-hexanoic acid (in place of the soya oil fatty acid) and no acetylacetone.

EXAMPLE 6

Example 1 was repeated using 512.2 g of erucic acid (in place of the soya oil fatty acid) and 10 g of acetylacetone.

EXAMPLE 7

| | |
|---|---|
| Aluminum Triisopropoxide: | 409 g |
| Ethylacetoacetate: | 260 g |
| Propan-2-ol: | 95.5 g |
| Water: | 40.3 g |
| Butan-2-ol: | 38.5 g |
| Methylethylketoxime: | 522.7 g |

The aluminum tri-isopropoxide was charged to a flask fitted with a stirrer, thermometer, nitrogen purge and a condenser for refluxing and distillation. Stirring was commenced and the aluminum tri-isopropoxide was heated to 90° C. The ethylacetoacetate was then added (over 2.5 hours) maintaining the temperature of the mixture at 90° C. On completion of addition, the mixture was held at 90° C. for 30 minutes. The mixture was then distilled until a vessel temperature of 150° C. was attained. The mixture was held at 150° C. for 30 minutes and then cooled to 85° C.

A mixture of the water and the propan-2-ol was then added (over 1.5 hours), the exothermic reaction being sufficient to maintain reflux without additional heating. On completion of addition, the reaction mixture was refluxed for 30 minutes. The mixture was then distilled until a vessel temperature of 150° C. was attained. The mixture was then held at 150° C. for 30 minutes.

The butan-2-ol was then added (over 30 minutes). During the addition, the vessel temperature falls to 110°–115° C. On completion of addition, the reaction mixture was held at 110°–115° C. for 30 minutes.

The mixture was then distilled until a vessel temperature of 150° C. was attained. A nitrogen bleed was used to help distillation. Vacuum (29 in.Hg) was then applied to the vessel and the reaction mixture distilled under vacuum at 150° C. for 30 minutes. The vessel was then returned to atmospheric pressure and the reaction mixture was cooled to 125° C. 50% of the methylethylketoxime was added which cooled the mixture to 75°–80° C. The mixture was held at 75°–80° C. for 30 minutes. The remaining methylethylketoxime was then added and the mixture cooled to 30°–40° C.

The aluminum complexes prepared as described as above were compared with standard driers in paint formulations based on the following high solids alkyd resins.

| | |
|---|---|
| **Cargill 57-5766** | |
| Type: | Long oil alkyd |
| Acid value (mg KOH/G) | 10.0 |
| Non volatile content: | 90.0% |
| Viscosity (Gardener): | Z1-Z3 |
| Solvents: | mineral spirits/xylene |
| **Beckosol 10-539** | |
| Type: | Pure drying Alkyd |
| Acid value (mg KOH/g): | 10.0 |
| Non volatile content: | 90.0% |
| Viscosity (Gardener): | Z1-Z3 |
| Solvent: | Mineral spirits |

High solids, high gloss paints were prepared from these alkyds according to the following formulations:

| | |
|---|---|
| Mill base | |
| High solids alkyd | 935.0 g |
| Titanium dioxide (RCL-535) | 1706.0 |
| White spirit | 212.0 |
| Let down | |
| High solids alkyd | 1395,0 g |
| White spirit | 482.8 |

The paints were prepared on a high speed disperser to produce paints with the following properties:

| | |
|---|---|
| Hegmann Value | 8.0 |
| Pigment:Binder ratio | 0.8:1.0 |
| Viscosity (25c) (poises) | 5.0 (Cargill)/7.0 (Beckosol) |

-continued

| | |
|---|---|
| Binder Content | 44.3% |
| Non volatile content | 84.2% |

In the Cargill-based paint a standard drier system incorporating a higher than normal level of zirconium was used. This standard system contained 0.08% cobalt, 0.2% calcium, 0.2% zirconium, based on weight of binder, and 0.2% by weight of the paint of anti-skinning agent, viz. methylethylketoxime. This standard system was tested and compared against unstabilized and stabilized aluminum complexes which were used at 0.08% cobalt and 0.1% aluminum based on weight of binder.

In the Beckosol-based paint, a standard drier system with a higher level of zirconium and lithium was used, as recommended by Reichhold (the Manufacturers of Beckosol) to improve the surface and through drying. The standard Beckosol system contained 0.06% cobalt, 0.03% lithium, 0.2% calcium and 0.2% zirconium by weight of binder and 0.2% by weight of paint of anti-skinning agent, i.e. methylethylketoxime. This was compared with systems containing stabilized and unstabilized aluminum which were used at 0.08% cobalt, 0.03% lithium and 0.1% aluminum by weight of binder. In this case the higher level of cobalt in conjunction with lithium was required to overcome the slight reduction in surface drying that occurred with the stabilized aluminum complexes.

The storage stability of both paint systems was assessed initially and after 1 month's storage at 50° C. The results showed that the stabilized aluminum complexes provided acceptable stability in the Cargill and Beckosol paints. The stability results are shown below.

| | Low Shear Viscosity (poises/25° C.) | |
|---|---|---|
| | Initial | 4 weeks at 50° C. |
| Cargill paints | | |
| Standard | 5 | 8.5 |
| Stabilized aluminum carboxylate complex of Example 2 | 5 | 10 |
| Stabilized polyoxo-aluminum complex of Example 7 | 5 | 12 |
| Unstabilized aluminum compound Alusec 588* | 8 | gelled |
| Beckosol paints | | |
| Standard | 14.5 | 21 |
| Stabilized aluminum carboxylate complex of Example 2 | 12.0 | 12.5 |
| Stabilized polyoxo-aluminum complex of Example 7 | 13.5 | 15.0 |
| Unstabilized aluminum compound Alusec 588* | 19.0 | gelled |

*Alusec 588 is a commercially available aluminum containing drier sold by Rhone-Poulenc Chemicals Ltd. containing 7.1% aluminum.

Beck Koller and Ballotini drying tests were carried out at 25° C. and 65% relative humidity at a film thicknesses of 75 microns. The Ballotini through drying time is an in-house developed test where a 200 micron wet paint film is allowed to surface dry. The paint film is then peeled back by fingernail and the films were classified "Ballotini through dry" when Ballotini would not stick to the surface. In this test Ballotini through drying times were carried out at 25° C. and 65% relative humidity. In general the aluminum containing systems increased the rate of through drying compared to the standard systems. In terms of gloss, embrittlement and yellowing resistance, there was no measurable difference between the systems.

An example of the increased through drying performance for the Cargill system is given below.

| Cargill Paints | Beck Koller (Stage 4) HOURS | Ballotini Through DAYS |
|---|---|---|
| Standard | 8.5 | 19 |
| Stabilized aluminum carboxylate complex of Example 2 | 3.2 | 13 |
| Stabilized polyoxo aluminum complex of Example 7 | 3.7 | 19 |

Using the Cargill 57-5766 alkyd a white, medium tint base was prepared. In this system a level of 0.6% zirconium in conjunction with 0.2% "Active 8" (38 % 1,10-phenanthroline in n-butanol and 2-ethyl-hexanoic acid from RT Vanderbilt Co. Inc.) is recommended by Cargill to produce adequate through drying. The standard system used contained 0.04% cobalt, 0.6% zirconium, 0.2% Active 8 based on binder and 0.1% anti-skinning agent based on the weight of the paint. This system was compared against the two stabilized aluminum systems using 0.04% cobalt and 0.1% aluminum for the stabilized aluminum carboxylate and 0.08% Co, 0.01% lithium and 0.1% aluminum for the stabilized polyoxo-aluminum compound.

| Millbase | |
|---|---|
| Cargill 57-5766 (high solids alkyd from Cargill Inc.) | 570.0 |
| Daniels XL1/80 (Dispersant, Daniel Products Co.) | 11.4 |
| Maximix 6 (calcium carbonate of Cyprus Industrial Minerals Corp.) | 153.1 |
| Minex 7 (sodium potassium aluminum silicate of Lindusmin Ltd.) | 357.7 |
| Titanium Dioxide (RCL 535 of SCM Chemicals) | 777.5 |
| White spirit (184 aromatics from Carless Refining and Marketing Co.) | 34.2 |
| Exxsol D40 (100% aliphatic from Exxon Chemicals Ltd.) | 79.8 |

This was dispersed to Hegmann 7.0 using a high speed disperser.

| Letdown | |
|---|---|
| Cargill 57-5766 | 2292.7 |
| Daniels XLI/80 | 4.6 |
| BYK 077 (defoamer from Byk-Chemie) | 11.4 |
| White spirit | 24.5 |
| Exxsol D40 | 57.2 |
| Solvesso 100 (100% aliphatic solvent) | 100.9 |

The letdown was slowly added to the mill base with stirring. This paint was then tinted with Hüls blue, red, black and green tinters (Hüls America Inc. colortrend 888 universal machine colorants) to produce strong colors ranging from binder contents of 54 to 58%. The final properties of the paint were:

Pigment:binder ratio: 0.5:1.0

Binder content: 54–58% depending on colorant used.

Volatile content: In the region of 236 g per liter.

The stabilized aluminum complex systems of the present invention produced adequate stability in all systems and improved the storage stability in the colored systems. This is shown below for the colored systems.

| | Low shear Viscosity (poises/25° C.) Initial/4 weeks at 50° C. | | | |
|---|---|---|---|---|
| | Red | Black | Green | Blue |
| Standard | 50/51 | 42/48 | 35/46 | 42/56 |
| Stabilized aluminum carboxylate of Example 2 | 41/36 | 37/35 | 32/29 | 30/33 |
| Stabilzed polyoxo-aluminum of Example 7 | 48/45 | 42/38 | 33/37 | 33/37 |

Beck-Koller drying times were carried out at 25° C. and 65% relative humidity at a film thicknesses of 75 microns. The Ballotini results were measured under laboratory conditions of approximately 16° C. The surface Ballotini results were carried out on 75 micron films, whilst the through Ballotini results were assessed at 200 microns. In general, the through and surface drying as well as the loss of dry on ageing of the aluminum systems were equivalent to the standard system, which contained 0.6% zirconium and 0.2% "Active 8". However, the surface drying of the polyoxo-aluminum complex system was improved. This was expected because this system had an increased cobalt level. In these systems there was no major differences in terms of gloss, yellowing resistance or embrittlement.

Using the Beckosol 10-539 alkyd resin, a white gloss exterior house paint was produced. The standard system recommended by Reichhold to dry this paint is 0.042% cobalt, 0.104% neodymium (Neochem 250 of Mooney Chemicals), 0.024% Vanadium and 0.012% potassium (Cur-RX of Mooney Chemicals), and 0.231% of 2,2-dipyridyl solution (Drymax of Huls American Inc.). This was compared against 0.08% cobalt, 0.1% Aluminum and 0.03% lithium using both the stabilized aluminum complexes.

| Mill base | |
|---|---|
| Beckosol 10-539 (High solids alkyd of Reichold Chemicals Inc.) | 1240 g |
| Daniels XLI/80 (Dispersant of Daniel Products Co.) | 39.9 |
| Titanium dioxide white pigment (RCL 535 of SCM Chemicals) | 1198.3 |
| Cetacarb OG (calcium carbonate of Croxton and Garry Ltd.) | 530.9 |
| Snowcal 10ML (calcium carbonate of Croxton and Garry Ltd.) | 267.2 |
| Nopcocide N96 (Biocide of Henkel) | 29.9 |

This was dispersed using a high speed disperser to Hegmann 6.

| Let Down | |
|---|---|
| Bentone pregel | 490.4 |
| Beckosol 10-539 | 644.8 |
| 40 poise stand oil brushing aid (Samuel Banners) | 299.8 |
| Exxsol D40 | 268.2 |
| White spirit | 16.9 |
| Bentons Pregel | |
| Exxsol D40 | 429.2 |
| White spirit | 27.0 |
| Bentone 38 (Steetley Minerals) | 73.3 |
| Mix well at low speed and add: | |
| Anti-terra U (Byk-Chemie) | 5.4 |
| Propylene Carbonate (Fluka Chemicals) | 1.39 |
| Mix at high speed until gelled. | |

This paint system was tinted with red, black, yellow and blue tinters to produce paints which had binder contents varying from 31 to 34%. The paints had the following properties:

Pigment:binder ratio: 1.1

Binder content: 31–34% depending on the colorant used.

Volatile content: In the region of 248 g per liter.

All the paints produced acceptable visco-stability and the rate of surface drying was quicker for the aluminum-containing systems than it was for the standard system. The increase in surface dry is probably due to the increased cobalt levels in these systems. In terms of through drying, equivalent results for the standard and aluminum-containing systems were obtained.

Surprisingly when the loss of dry on ageing (1 month at 50° C. at 76 microns) was tested for the standard neodymium systems, it was found that all the tinted paints were still wet to touch after 48 hours drying at 25° C./65% relative humidity, whereas the stabilized aluminum systems were touch dry in less than 24 hours. In the white systems the neodymium system performed to the same extent as the stabilized aluminum systems producing surface drying times of 5 hours and through drying times of 20 hours. In all of the systems there was no major differences in terms of gloss, yellowing resistance or embrittlement.

The invention accordingly includes within its scope compositions, especially paint compositions and more particularly those having a high solids content preferably based on a synthetic resin, and especially an air drying alkyd resin comprising, as a cross-linker (drier) for the binder, an aluminum complex containing an oxime as described above.

We claim:

1. A coating composition comprising an air-drying alkyd resin binder and a cross-linking agent consisting of an aluminum complex, said aluminum complex formed by a process comprising the steps of:

(a) forming an aluminum product having aluminum coordination sites by reacting (i) an aluminum alcoholate or phenolate with (ii) an enolizable β-diketo compound or a carboxylic acid; and (b) forming the aluminum complex by reacting said aluminum product with a volatile ketoxime or aldoxime compound, the proportion of said volatile ketoxime or aldoxime compound being sufficient to complex all of the aluminum coordination sites in said aluminum product.

2. An aluminum complex formed by a process comprising the steps of:

(a) forming an aluminum product having aluminum coordination sites by reacting (i) an aluminum alcoholate or phenolate with (ii) an enolizable β-diketo compound or a carboxylic acid; and (b) forming the aluminum complex by reacting said aluminum product with a volatile ketoxime or aldoxime compound, the proportion of said volatile ketoxime or aldoxime compound being sufficient to complex all of the aluminum coordination sites in said aluminum product.

3. An aluminum complex according to claim 2, wherein said reaction in step (a) is conducted in the presence of water.

4. An aluminum complex according to claim 2, wherein said volatile ketoxime or aldoxime compound has from 2 to 6 carbon atoms.

5. An aluminum complex according to claim 4, wherein said volatile ketoxime or aldoxime compound is methlethylketoxime.

* * * * *